United States Patent
Farrell et al.

(10) Patent No.: US 10,569,047 B2
(45) Date of Patent: Feb. 25, 2020

(54) WATER DISINTEGRABLE FLUSHABLE CATHETER

(71) Applicant: Hollister Incorporated, Libertyville, IL (US)

(72) Inventors: David J. Farrell, Ballina (IE); John T. Clarke, Galway (IE)

(73) Assignee: Hollister Incorporated, Libertyville, IL (US)

( * ) Notice: Subject to any disclaimer, the term of this patent is extended or adjusted under 35 U.S.C. 154(b) by 114 days.

(21) Appl. No.: 15/736,435

(22) PCT Filed: Jun. 7, 2016

(86) PCT No.: PCT/US2016/036223
§ 371 (c)(1),
(2) Date: Dec. 14, 2017

(87) PCT Pub. No.: WO2016/205018
PCT Pub. Date: Dec. 22, 2016

(65) Prior Publication Data
US 2018/0169381 A1      Jun. 21, 2018

Related U.S. Application Data

(60) Provisional application No. 62/180,954, filed on Jun. 17, 2015.

(51) Int. Cl.
| | | |
|---|---|---|
| A61M 25/00 | (2006.01) | |
| A61L 29/08 | (2006.01) | |
| A61L 29/14 | (2006.01) | |
| A61L 29/04 | (2006.01) | |

(52) U.S. Cl.
CPC ....... *A61M 25/0045* (2013.01); *A61L 29/043* (2013.01); *A61L 29/085* (2013.01); *A61L 29/14* (2013.01); *A61L 29/148* (2013.01); *A61L 2400/10* (2013.01)

(58) Field of Classification Search
CPC ......... A61M 25/0045; A61L 29/085; A61L 29/148; A61L 29/043; A61L 29/14; A61L 2400/10
See application file for complete search history.

(56) References Cited

U.S. PATENT DOCUMENTS

| | | |
|---|---|---|
| 5,681,873 A | 10/1997 | Norton et al. |
| 5,762,638 A | 6/1998 | Shikani et al. |
| 5,789,018 A | 8/1998 | Engelson et al. |
| 5,800,412 A | 9/1998 | Zhang et al. |

(Continued)

FOREIGN PATENT DOCUMENTS

| | | |
|---|---|---|
| EP | 0693948 | 7/1998 |
| EP | 1415671 | 5/2004 |

(Continued)

OTHER PUBLICATIONS

International Search Report and Written Opinion of the International Searching Authority dated Sep. 9, 2016, for International Application No. PCT/US2016/036223.

(Continued)

*Primary Examiner* — Michael C Miggins
(74) *Attorney, Agent, or Firm* — Cook Alex Ltd.

(57) ABSTRACT

A water disintegratable catheter having a barrier layer disposed on an outer surface and/or inner surface of the catheter wherein the barrier layer comprises a hydrophobic component.

15 Claims, 1 Drawing Sheet

(56) References Cited

U.S. PATENT DOCUMENTS

| | | |
|---|---|---|
| 6,096,809 A | 8/2000 | Lorcks et al. |
| 6,235,816 B1 | 5/2001 | Lorcks et al. |
| 6,533,854 B2 | 3/2003 | Kesselring et al. |
| 6,706,025 B2 | 3/2004 | Engelson et al. |
| 6,878,199 B2 | 4/2005 | Bowden et al. |
| 7,008,979 B2 | 3/2006 | Schottman et al. |
| 7,112,298 B2 | 9/2006 | Kampa et al. |
| 8,143,368 B2 | 3/2012 | Domb et al. |
| 8,168,249 B2 | 5/2012 | Utas et al. |
| 8,187,254 B2 | 5/2012 | Hissink et al. |
| 8,241,656 B2 | 8/2012 | Chudzik et al. |
| 8,569,402 B2 | 10/2013 | Henderson et al. |
| 8,907,155 B2 | 12/2014 | Wang et al. |
| 2005/0283111 A1 | 12/2005 | Maurice |
| 2011/0071507 A1 | 3/2011 | Svensson et al. |
| 2012/0316515 A1 | 12/2012 | Terry |
| 2015/0110759 A1 | 4/2015 | Suzuki et al. |

FOREIGN PATENT DOCUMENTS

| | | |
|---|---|---|
| EP | 1327663 | 5/2007 |
| EP | 1556097 | 8/2011 |
| EP | 1926509 | 1/2012 |
| EP | 1937327 | 4/2012 |
| EP | 1745807 | 8/2012 |
| EP | 2279767 | 8/2012 |
| EP | 1955724 | 12/2012 |
| EP | 1499667 | 8/2013 |
| EP | 2301595 | 1/2014 |
| WO | WO 9426336 | 11/1994 |
| WO | WO 9815301 | 4/1998 |
| WO | WO 0039213 | 7/2000 |
| WO | WO 03028783 | 4/2003 |
| WO | WO 03059756 | 7/2003 |
| WO | WO 03093357 | 11/2003 |
| WO | WO 2004039424 | 5/2004 |
| WO | WO 2006002103 | 1/2006 |
| WO | WO 2006037157 | 4/2006 |
| WO | WO 2006071813 | 7/2006 |
| WO | WO 2007011287 | 1/2007 |
| WO | WO 2007035886 | 3/2007 |
| WO | WO 2007040557 | 4/2007 |
| WO | WO 2009020455 | 2/2009 |
| WO | WO 2011036162 | 3/2011 |
| WO | WO 2011079129 | 6/2011 |
| WO | WO 2012066436 | 5/2012 |
| WO | WO 2014077886 | 5/2014 |
| WO | WO 2015069843 | 5/2015 |

OTHER PUBLICATIONS

Drinkwater, A et al., "Test Protocol to Determine the Flushability of Disposable Products"; UKWIR Project WM07G202; Mar. 2012.

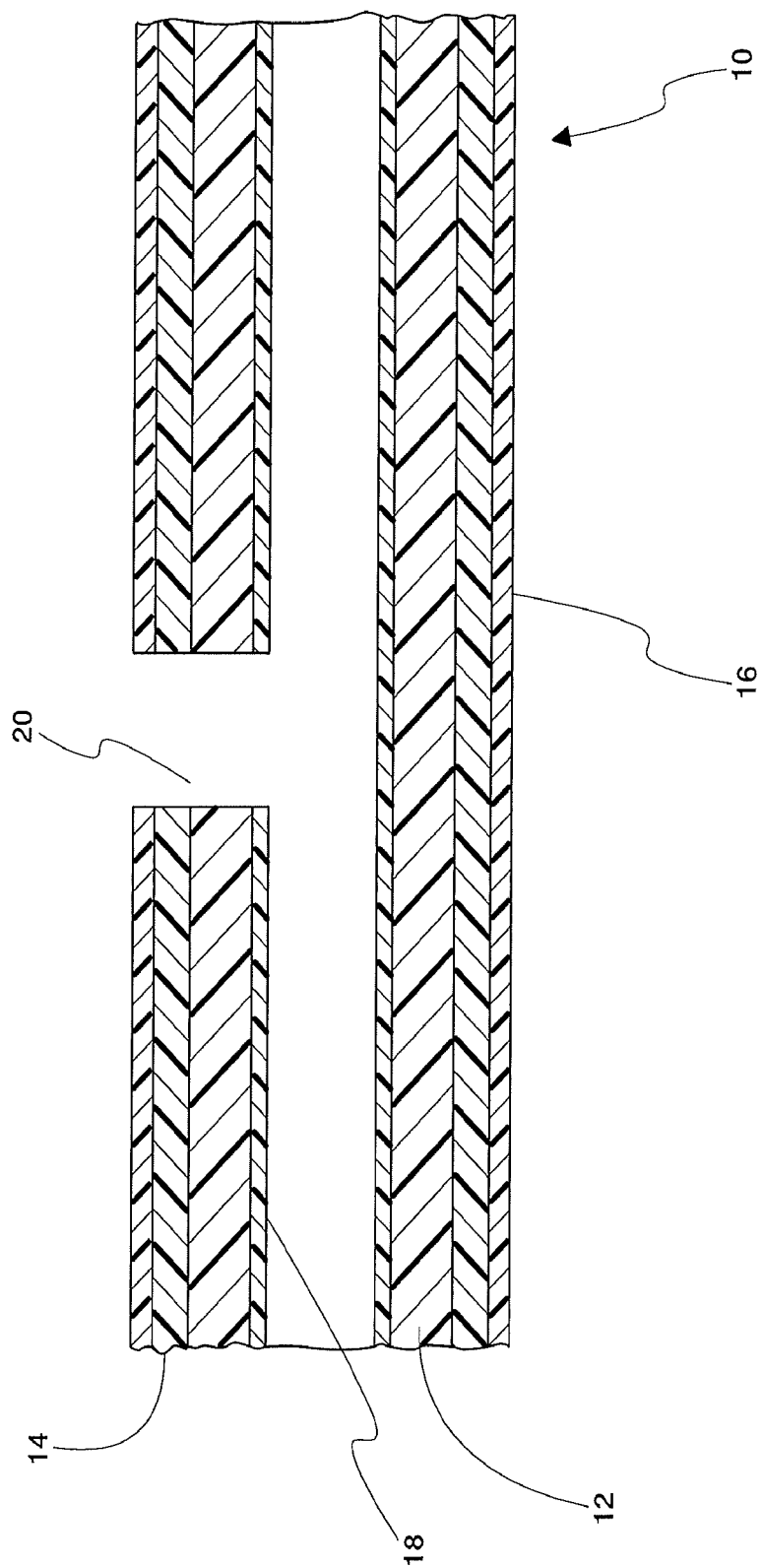

WATER DISINTEGRABLE FLUSHABLE CATHETER

This is a U.S. National Stage of PCT International Patent Application No. PCT/US2016/036223, filed Jun. 7, 2016, which claims the benefit and priority to U.S. Provisional Patent Application No. 62/180,954, filed Jun. 17, 2015, both of which are hereby incorporated herein by reference.

FIELD OF THE DISCLOSURE

The present disclosure is directed to flushable products and, more particularly, to flushable urinary catheters that include water disintegrable catheter tubes having a water barrier layer disposed thereon to impede water ingress into the water disintegrable material of the catheter tube during use of the catheter. The barrier layer may also serve as a support or attachment layer for a lubricous hydrophilic coating that reduces friction to allow for easier and less traumatic insertion of the catheter into and through the user's urethra.

BACKGROUND

Flushable urinary catheter products made from water disintegrable materials are desirable because such catheters may be disposed of after use by flushing the catheter down the toilet. It is also desirable for urinary catheters to include a lubricous hydrophilic coating that becomes lubricous when wetted with a wetting fluid, such as water. Such lubricious hydrophilic coatings ease the insertion and removal of the catheter into and out of the patient.

However, hydrophilic coatings can be problematic for water disintegrable catheters because they typically require wetting with water to hydrate the coating. While the coating will become lubricious upon hydration, the water disintegrable material of the catheter may start to degrade and eventually become mechanically unstable. Thus, the water disintegrable catheter when in substantial contact with water eventually may not support catheter functionality and may not support the hydrophilic coating during use. For instance, as the catheter breaks down, the hydrophilic coating may become unstable and may not suitably adhere to the catheter. This can result in premature weakening of the catheter structure and separation of the hydrophilic coating from the catheter during use.

SUMMARY

The present disclosure provides flushable catheters that include water barrier layers. The water barrier layer impedes the ingress of water into the water disintegrable material of the catheter during use and also may act as a support or bonding layer for a lubricious hydrophilic coating. The water barrier layer may be disposed on the outer surface and/or inner surface of a catheter shaft made from water disintegrable material to impede the ingress of water into such disintegrable material. A barrier layer disposed on the inner surface of the catheter shaft may inhibit bodily fluids (e.g., urine) from coming into contact with the disintegrable material of the catheter shaft as such fluids pass through the shaft. A barrier layer disposed on the outer surface of the catheter shaft may also inhibit bodily fluids from coming into contact with the water disintegrable material of the shaft. As mentioned above, a barrier layer on the outer surface of the catheter shaft may also serve as a support or attachment layer for a lubricious hydrophilic coating. When used to support a lubricous hydrophilic coating, the barrier layer also inhibits the wetting agent, such as water, from coming in contact with the disintegrable material of the catheter tube.

The water disintegratable urinary catheters disclosed herein are those that structurally breakdown when contacted by water. Because of the water disintegratable characteristics such catheters can be conveniently disposed down a toilet and through the sewer system. The water disintegrable catheters may be made from one or more materials that are affected by a fluid (for example, water, urine or fluids utilized in toilet and plumbing systems). Such materials may be water disintegratable or disintegrable materials. As used herein "water disintegratable" or "water disintegrable" materials refer to materials that are water soluble, water degradable, or water hydrolysable, and which dissolve, degrade, or otherwise breakdown when in contact with water over a selected period of time. The materials and physical structures thereof may be tailored to partially or fully breakdown depending on the desired use. In other embodiments, the material may be enzymatically hydrolysable. The water disintegratable and enzymatically hydrolysable materials are preferably flushable materials which are suitable for disposal in a toilet or sanitary system and, even more preferably, biodegradable flushable materials which may be chemically broken down by living organisms or other biological means.

In one embodiment, the water disintegrable, flushable catheter has a catheter shaft that is made from a water disintegratable material, such as polyvinyl alcohol (PVOH), wherein the outer surface of the catheter shaft is coated with a water barrier layer that will support a lubricious hydrophilic coating even when the hydrophobic coating is wetted with, for example, water or an aqueous solution. The water barrier layer may adhere well to the water disintegrable catheter shaft and to the lubricious hydrophilic coating applied on top of the water barrier layer. As mentioned above, such a water barrier layer allows the hydrophilic coating to be hydrated while preventing or limiting water molecules from attacking the PVOH catheter shaft. Without the water barrier layer, the wetting fluid used to wet the hydrophilic coating could come into contact with the PVOH catheter shaft and begin to prematurely degrade the catheter shaft. Premature degradation of the shaft undesirably increases the risk of the hydrophilic coating detaching from the shaft prior to or during use. In the catheters of the present disclosure, the water barrier layers prevent or limit water from contacting the PVOH catheter shaft, reducing the risk of the hydrophilic coating detaching from the shaft.

The barrier layer may include a hydrophobic component, such as ethyl cellulose. The barrier layer may also include one or more hydrophilic components, such as a hydrophilic polymer, blended or combined with the hydrophobic component(s) of the barrier layer. Such hydrophilic component may be used to increase the hydrophilicity of the barrier layer and/or to attenuate or vary the amount of water ingress into the water disintegratable material and/or tailor the disintegration rate of the barrier layer. In one example, the barrier layer composition may be made from a combination of hydrophobic and hydrophilic components wherein the barrier layer is primarily formed from hydrophobic components. In one embodiment, the barrier layer coating may include a combination of hydrophobic ethyl cellulose and hydrophilic hydroxyl propyl methyl cellulose and/or poly (ethylene glycol) diacrylate (PEGDA). The barrier layer coating may also include other agents, such as those that assist in adhesion to the catheter and/or the hydrophilic coating.

The barrier layer may be applied to the catheter by, for example, dip coating, spraying or painting the coating on the catheter and then allowing the coating to dry and/or cure. The barrier layer coating formulation may include any suitable carrier solvent, such as ethanol, in which the components of the barrier layer coating are dissolved to form the coating solution. The formulation may also include crosslinkers and UV curing agents.

Depending on the desired effect and use, the barrier layer may be tailored to allow a selected rate of water ingress. For example, the barrier layer may temporarily substantially prevent the ingress of water for a relatively short period of time or under selected conditions, after which the barrier breaks down to allow ingress of water into the disintegrable material. In other embodiments, the barrier layer may be tailored to remain intact for longer periods of time and substantially prevent the ingress of water for such longer periods. In still other embodiments, the barrier layer may be tailored to allow a continuous flow of water therethrough at a desired rate.

Optionally, the inner surface of the catheter shaft may also be coated with an inner water barrier layer, which may be made of the same formulation of the outer water barrier layer or may be made from a different formulation. The inner barrier impedes urine or other fluids from coming into contact with the catheter shaft.

When the water disintegrable material of the catheter is a material that swells when the in contact with water, the preventing or limiting of the ingress of water into the water disintegratable material by the water barrier layer can also reduce/prevent the swelling of the water disintegratable material during use and can prevent/reduce the rate of disintegration of the water disintegratable material during use.

In one aspect, the present disclosure provides a water disintegrable, flushable catheter having a water disintegrable catheter shaft made from a water disintegrable material, such as PVOH, wherein the shaft is coated with a water barrier layer. The water barrier layer may include a hydrophobic component, such as ethyl cellulose. The water barrier layer may act as a water barrier that impedes or limits the ingress of water into the water disintegrable material of the catheter shaft during use. The water barrier layer, optionally, may also act as a stable support or attachment layer for a lubricious hydrophilic coating. Additionally, the water barrier layer also may be tailored or attenuated to limit the rate of ingress of water into the water disintegrable material of the catheter shaft. For example, the water barrier layer may also include an amount of a hydrophilic component which increases the ingress of water through the barrier.

BRIEF DESCRIPTION OF THE DRAWING

FIG. 1 is a longitudinal cross-section of a portion of a catheter tube having a water barrier layer according to the present disclosure.

DETAILED DESCRIPTION OF THE EMBODIMENTS

The present disclosure relates to a water disintegrable flushable product, such as a medical product, that will dissolve, hydrolyze or biodegrade in water. The medical product may be, for example, a urinary catheter. While the subject matter described herein is described relative to a flushable urinary catheter, it will be understood that the subject matter is applicable to other flushable devices and products as well.

The urinary catheters of the present disclosure are made from a water disintegrable material(s). The urinary catheters also include a water barrier layer disposed on the inner and/or the outer surfaces of the catheter shaft. The water barrier layer prevents or limits the ingress of water to the water disintegrable material for a desired time period. As explained in more detail below, the water barrier may be a coating that is applied over the inner and/or outer surfaces of the catheter. The water barrier layer is preferably biodegradable. Additionally, the water barrier layer, optionally, supports or is an attachment for a lubricous hydrophilic coating, when one is used on the catheter.

FIG. 1 illustrates a portion of a catheter 10 according to the present disclosure. The catheter includes a catheter shaft tube 12, which is made of a water disintegratable material. A water barrier layer, such as water barrier coating 14, is disposed on the outer surface of the catheter shaft 12. A lubricous hydrophilic coating 16 is disposed on the barrier coating 14. Optionally, a barrier coating 18 may be disposed on the inner surface of the catheter shaft tube. A radial eyelet 20 may be located in the catheter shaft tube 12 for the drainage of urine through the tube. A suitable tip (not shown) will be formed at the right end (as seen in FIG. 1) of the tube.

The catheter shaft may be made from one or more water (for example, water, urine or fluids utilized in toilet and plumbing systems) disintegrable materials. Such material may include, for example, water soluble, water hydrolysable or enzymatically hydrolysable materials, which at least partially dissolve or breakdown when in contact with water. The material of the catheter shaft may be designed to partially or fully dissolve and/or breakdown depending on the desired use. The water disintegrable materials are preferably flushable materials which are suitable for disposal in a toilet or sanitary system and, even more preferably, biodegradable flushable materials which may be chemically broken down over time by water, living organisms or other biological means.

Such water disintegrable materials may include, for example, polyvinyl alcohol, including but not limited to an extrudable polyvinyl alcohol, polyacrylic acids, polylactic acid, polyesters, polyglycolide, polyglycolic acid, poly lactic-co-glycolic acid, polylactide, amines, polyacrylamides, poly(N-(2-Hydroxypropyl) methacrylamide), starch, modified starches or derivatives, amylopectin, pectin, xanthan, scleroglucan, dextrin, chitosans, chitins, agar, alginate, carrageenans, laminarin, saccharides, polysaccharides, sucrose, polyethylene oxide, polypropylene oxide, acrylics, polyacrylic acid blends, poly(methacrylic acid), polystyrene sulfonate, polyethylene sulfonate, lignin sulfonate, polymethacrylamides, copolymers of aminoalkyl-acrylamides and methacrylamides, melamine-formaldehyde copolymers, vinyl alcohol copolymers, cellulose ethers, poly-ethers, polyethylene oxide, blends of polyethylene-polypropylene glycol, carboxymethyl cellulose, guar gum, locust bean gum, hydroxyproply cellulose, vinylpyrrolidone polymers and copolymers, polyvinyl pyrrolidone-ethylene-vinyl acetate, polyvinyl pyrrolidone-carboxymethyl cellulose, carboxymethyl cellulose shellac, copolymers of vinylpyrrolidone with vinyl acetate, hydroxyethyl cellulose, gelatin, poly-caprolactone, poly(p-dioxanone), or combinations, blends or co-polymers of any of the above materials. The water disintegrable or enzymatically hydrolysable materials may also be any of those that are included in certified flushable products that meet the National Sanitation Foundation standards for flushability or materials and products that meet INDA/EDANA Flushability Guidelines or the UK Water Industry Research, test protocols set forth in "Test Protocol to Determine the Flushability of Disposable Products, Review of the Manufactures $3^{rd}$ Ed. Guidance Document," 2013, by Drinkwater et al. While catheters made from water disintegrable or enzymatically hydrolysable materials may be disposed of in a toilet, it is not necessary to dispose of such catheters in a toilet and such catheters may also be disposed in normal municipal waste systems or garbage collection systems.

The water barrier layer may include one or more hydrophobic polymers. The hydrophobic polymers may include, for example, hydrophobic celluloses, ethyl cellulose, acrylates, methyl acrylate-methacrylic acid copolymers, methyl methacrylate-methacrylic acid copolymers, beeswax and/or other suitable waxes, chitosan, plastarch material (PSM), poly-3-hydroxybutyrate (PHB), polyhydroxyalkanoate (PHA), polycaprolactone, polyvinyl acetate phthalate (PVAP), shellac, sodium alginate, alginates, zein or combinations thereof.

The water barrier layer may also include one or more hydrophilic components, such as a water soluble polymer, blended or combined with the hydrophobic components. The hydrophilic components may include for example, hydroxyl propyl methyl cellulose, poly(ethylene glycol) (PEG), PEG DA, oly(N-isopropylacrylamide) (PNIPAM), polyacrylamide (PAM), poly(2-oxazoline), polyethylenimine (PEI), acrylic polymers, poly(acrylic acid), polymethacrylate, poly(ethylene oxide), poly(vinyl alcohol) (PVA), PVA copolymers, poly(vinylpyrrolidone) (PVP) and PVP copolymers, polyelectrolytes, maleic anhydride copolymers, polyethers, cucurbit[n]uril hydrate, hyaluronic acid (HA), albumin and copolymers, mixtures and bends of the above. Furthermore, the hydrophilic components may be hydrophilic polymers that are formed within the barrier layer by inclusion of reactive monomers (such as PEGDA, HEMA, Acrylic Acid, Methacrylic Acid) and combinations of monomers (such as acrylate & methacrylate monomers) and an appropriate initiator system (triggered by heat, light or other means). Such monomers may yield cross-linked polymers or linear polymers or variations thereof.

Other hydrophilic additives that may help achieve the desired degrees of film porosity could include ethyl cellulose type films prepared as dispersions with water soluble organic and inorganic salts or compounds.

Such hydrophilic components may be used to increase the hydrophilicity of the barrier layer and/or to attenuate or vary the amount of water ingress into the water disintegratable material and/or tailor the disintegration rate of the barrier. For example, the hydrophilic component may be used to tailor or attenuate the porosity of the hydrophobic barrier layer. In one embodiment, the hydrophilic barrier is a porous polymer coating wherein the coating includes a desired amount of the hydrophilic component to tailor the porosity of the coating.

In one embodiment of a water barrier layer, the hydrophobic component may be between about 75 wt % and about 100 wt % of the water barrier layer and the hydrophilic component may be between about 0 wt % and about 25 wt % of the water barrier layer. In another embodiment, the hydrophobic component is between about 80 wt % and about 90 wt % of the water barrier layer and the hydrophilic component is between about 10 wt % and about 20 wt % of the water barrier layer. In another embodiment, the hydrophobic component is about 85 wt % of the water barrier layer and the hydrophilic component is about 15 wt % of the water barrier layer.

The thickness of the water barrier layer may vary depending on the desired use. For example, the thickness of the water barrier layer may be selected to tailor the rate of disintegration of the barrier and/or the rate of water passing through the barrier. In one embodiment, the thickness of the water barrier layer may be at least about 1 micron. In another embodiment, the thickness of the barrier layer may be less than about 1000 microns. In one example, the thickness of the water barrier layer may be between about 1 micron and about 1000 microns. In another example, the thickness of the water barrier layer may be between about 10 microns and about 600 microns. In yet another example, the thickness of the water barrier layer may be between about 600 microns and about 1000 microns. In other examples, the thickness of the barrier layer may be less than about 1 micron or greater than 1000 microns.

Preferably, the barrier layer partially or totally disintegrates after use and while in the sewer system and water treatment plants. The level of disintegration of the barrier layer can be achieved by tailoring the relative solubility of the barrier layer by including hydrophilic components or other additives/agents in the barrier layer.

The disintegration rate of the barrier layers can also be achieved by tailoring the mechanical properties of the barrier layer. The mechanical properties of the barrier can be modified by increasing or decreasing the amount of cross-linking in the barrier. The properties may also be modified by differing the molecular weight and/or layer thickness. For example, a thin barrier layer may breakdown (disintegrate) to the desired particle size simply as a result of the physical action of flushing and the exposure to mechanical forces in sewage pipes and water treatment plants.

In addition, the balance between catheter disintegration and barrier breakdown rate can also be further tailored by using multiple layers of different barriers so as to create a functionality gradient. Relative solubility and mechanical strength can be used in tandem in order to achieve the desired breakdown rates for the barrier layers.

The barrier layer also may be tailored such that the catheter shaft remains protected from the ingress of water for a selected period of time. For example, the barrier layer may be tailored such that the catheter may be used for a period of time before the functionally of the catheter diminishes due to the ingress of water causing disintegration of the catheter shaft. In one embodiment, the barrier layer is tailored to protect against the ingress of water during the time period it takes for the user to complete catheterization.

In one embodiment, the barrier layer and catheter will disintegrate in such a manner as to meet the specifications for flushable products detailed in the "Test Protocol to Determine the Flushability of Disposable Products UKWIR Project WM07G202".

The barrier layer may also include agents that enhance adhesion of the layer to the catheter. For example, the agents may add functionality to the coating. In one embodiment, the barrier layer may include a photo-curable acrylate and photo-initiator to promote curing of same.

In one example of a flushable catheter, the catheter shaft is made from a water soluble flushable PVOH. The catheter shaft also includes a water barrier layer and a hydrophilic coating that may be activated by hydration. The catheter may be used by the end-user during a defined functional period, e.g. 20-30 minutes, after which the catheter can be disposed of conveniently and hygienically by flushing down the toilet.

The water barrier layer may be a coating applied to the outer and/or inner surfaces of the catheter shaft using any suitable coating processes, such as dip coating, spraying or painting a barrier solution onto the surfaces of the catheter shaft. After the barrier coating solution has been coated onto the surfaces of the catheter shaft, the coating solution may be dried and/or cured to form the water barrier layer. In a dip coating process, for example, the catheter shaft may be dipped into a barrier coating solution. After the catheter shaft is removed from the coating solution, the solution may be dried and/or cured to form the coating on the surface of the catheter shaft. The barrier coating may be adhered to the surface of the catheter by physical adhesion or chemical bonding. In one embodiment, the barrier coating may be fixed to the surface of the catheter by curing or fixed by heat, light or any other suitable manner. The barrier coating may be applied to the entire outer and/or inner surfaces of the catheter shaft or may be selectively applied to the surfaces wherein selected portions of the surface are coated while other portions remain uncoated.

In one embodiment of a water barrier coating solution, the coating solution formulation may include between about 0.75% and about 6% by weight of a hydrophobic component(s), such as ethyl cellulose, and between about 94 wt % to about 99.25 wt % solvent, such as ethanol. Optionally, the formulation may include between about 0.75 wt % and 4.25 wt % of a hydrophilic component, for example PEG DA such as PEG 400 DA, and about 0.20 wt % of a photoinitiator, such as Irgacure. In one embodiment of the water barrier coating solution, the hydrophobic component may be between about 0.75 wt % and about 6 wt %, the hydrophilic component may be between about 0.75 wt % and about 4.25 wt % and the solvent may be between about 89.75 wt % and about 98.5 wt % of the water barrier coating solution.

EXAMPLES

Listed below are exemplary barrier coating formulations:

| Formulation | Ethyl Cellulose wt % | PEG400DA wt % | Irgacure 2959 wt % | Ethanol wt % |
|---|---|---|---|---|
| 1 | 5.0 | — | — | 95 |
| 2 | 4.25 | 0.75 | 0.20 | 94.80 |
| 3 | 0.75 | 4.25 | 0.20 | 94.80 |

Aspects of the present subject matter described above may be beneficial alone or in combination with one or more other aspects. Without limiting the foregoing description, in accordance with a first aspect, a water disintegrable urinary catheter comprising a catheter shaft formed from a water disintegrable material; and a water barrier layer disposed on an outer surface of the catheter shaft, wherein the water barrier layer comprises a hydrophobic component.

Aspect 2. The catheter of aspect 1 further including a lubricious hydrophilic coating disposed on the water barrier layer.

Aspect 3. The catheter of any of the preceding aspects wherein the water barrier layer is a coating on the outer surface.

Aspect 4. The catheter of any of the preceding aspects wherein the hydrophobic component of the water barrier layer comprises a hydrophobic polymer.

Aspect 5. The catheter of any one of the preceding aspects wherein the hydrophobic component of the water barrier layer comprises ethyl cellulose.

Aspect 6. The catheter of any one of the preceding aspects wherein the water barrier layer comprises a hydrophilic component.

Aspect 7. The catheter of aspect 6 wherein the hydrophobic polymer is between about 80 wt % and about 90 wt % of the water barrier layer and the hydrophilic component is between about 10 wt % and about 20 wt % of the water barrier layer.

Aspect 8. The catheter of any one of aspects 6 and 7 wherein the hydrophobic polymer is about 85 wt % of the water barrier layer and the hydrophilic component is about 15 wt % of the water barrier layer.

Aspect 9. The catheter of any one of aspect 6-8 wherein the hydrophilic component of the water barrier layer comprises hydroxyl propyl methyl cellulose, poly(ethylene glycol) and/or poly(ethylene glycol) diacrylate.

Aspect 10. The catheter of any one of the preceding wherein the water disintegratable material of the catheter comprises polyvinyl alcohol.

Aspect 11. The catheter of any one of the preceding aspects wherein the water barrier layer has a thickness of between about 1 micron and about 1000 microns.

Aspect 12. The catheter of any one of the preceding aspects wherein the water barrier layer has a thickness of between about 600 microns and about 1000 microns.

Aspect 13. The catheter of any of one aspects 1-11 wherein the water barrier layer has a thickness of between about 10 microns and about 600 microns.

Aspect 14. The catheter of any one of the preceding aspects wherein the water barrier layer comprises a reactive monomer or oligomer.

Aspect 15. The catheter of any one of the preceding aspects further including a second water barrier layer disposed on an inner surface of the catheter shaft.

Aspect 16. A water barrier solution for forming a water barrier layer, the solution comprising: a solvent and a hydrophobic component.

Aspect 17. The water barrier solution of aspect 16 wherein the hydrophobic component comprises ethyl cellulose.

Aspect 18. The water barrier solution of any one of aspects 16 and 17 further comprising a hydrophilic component.

Aspect 19. The water barrier solution of any one of aspects 16-18 wherein the hydrophilic component comprises hydroxyl propyl methyl cellulose, poly(ethylene glycol) and/or poly(ethylene glycol) diacrylate.

Aspect 20. The water barrier solution of any one of the aspects 18-19 wherein the hydrophobic components are between about 0.75 wt % and about 6 wt %, the hydrophilic components are between about 0.75 wt % and about 4.25 wt %, and the solvent is between about 89.75 wt % and about 98.5 wt % of the water barrier solution.

Aspect 21. The water barrier solution of any one of aspects 16-20 further including a reactive monomer and/or oligomer.

It should be understood that various changes and modifications to the presently preferred embodiments described herein will be apparent to those skilled in the art. Such changes and modification can be made without departing from the spirit and scope of the invention disclosed herein.

The invention claimed is:

1. A water disintegrable catheter comprising:
   a catheter shaft formed from a water disintegrable material;
   a water barrier layer disposed on an outer surface of the catheter shaft, wherein the water barrier layer comprises a hydrophobic component; and
   a lubricious hydrophilic coating disposed on the water barrier layer.

2. The catheter of claim 1 wherein the water barrier layer is a coating on the outer surface.

3. The catheter of claim 1 wherein the hydrophobic component of the water barrier layer comprises a hydrophobic polymer.

4. The catheter of claim 1 wherein the hydrophobic component of the water barrier layer comprises ethyl cellulose.

5. The catheter of claim 1 wherein the water disintegratable material of the catheter comprises polyvinyl alcohol.

6. The catheter of claim 1 wherein the water barrier layer has a thickness of between about 1 micron and about 1000 microns.

7. The catheter of claim 1 wherein the water barrier layer has a thickness of between about 600 microns and about 1000 microns.

8. The catheter of claim 1 wherein the water barrier layer has a thickness of between about 10 microns and about 600 microns.

9. The catheter of claim 1 wherein the water barrier layer comprises a reactive monomer or oligomer.

10. The catheter of claim 1 further including a second water barrier layer disposed on an inner surface of the catheter shaft.

11. The catheter of claim 1 wherein the catheter shaft comprises a urinary catheter shaft.

12. (presented presented) The catheter of claim 1 wherein the water barrier layer comprises a hydrophilic component.

13. The catheter of claim 12 wherein the hydrophobic polymer is between about 80 wt% and about 90 wt% of the water barrier layer and the hydrophilic component is between about 10 wt% and about 20 wt% of the water barrier layer.

14. The catheter of claim 12 wherein the hydrophobic polymer is about 85 wt% of the water barrier layer and the hydrophilic component is about 15 wt% of the water barrier layer.

15. The catheter of claim 12 wherein the hydrophilic component of the water barrier layer comprises hydroxyl propyl methyl cellulose, poly(ethylene glycol) and/or poly(ethylene glycol) diacrylate.

* * * * *